United States Patent [19]

Gironda

[11] Patent Number: 5,599,827
[45] Date of Patent: Feb. 4, 1997

[54] STABLE MICROEMULSIONS OF CERTAIN 3-ISOTHIAZOLONE COMPOUNDS

[75] Inventor: Kevin F. Gironda, Alpha, N.J.

[73] Assignee: Rohm and Haas Company, Philadelphia, Pa.

[21] Appl. No.: 441,890

[22] Filed: May 16, 1995

[51] Int. Cl.$^6$ .................................................. A01N 43/80
[52] U.S. Cl. ......................... 514/372; 548/101; 548/213
[58] Field of Search ........................... 514/372; 548/101, 548/213

[56] References Cited

U.S. PATENT DOCUMENTS 4,954,338  9/1990  Mattox ...................................... 424/78
5,153,213  10/1992  Schmidt ................................. 514/372
5,444,078  8/1995  Yu ........................................... 514/372

*Primary Examiner*—Terressa Mosley
*Attorney, Agent, or Firm*—Julie J. L. Cheng

[57] ABSTRACT

Dilute solutions of 0.5 to about 5% by weight of at least one 3-isothiazolone selected from the group consisting of 5-chloro-2-methyl-4-isothazolin-3-one and 2-methyl-4-isothazolin-3-one are stabilized without using inorganic metal salts or hydrogen peroxide by forming a microemulsion composition with organic solvent(s) having less than 6 percent by weight solubility in water; anionic surfactant(s); and optionally, non-ionic surfactant(s).

8 Claims, No Drawings

STABLE MICROEMULSIONS OF CERTAIN 3-ISOTHIAZOLONE COMPOUNDS

This invention relates to stabilizing 5-chloro-2-methyl-4-isothazolin-3-one (5-chloro-2-methyl-3-isothiazolone or "CMI"); 2-methyl-4-isothazolin-3-one (2-methyl-3-isothiazolone or "MI") biocide compounds; or mixtures thereof, in dilute aqueous solutions.

Dilute aqueous solutions, or "dilute solutions," comprise 0.5 to 5% by weight of the aforementioned compound(s) dissolved in water, typically with no organic solvent present. The conventional stabilizing system for those compounds in such dilute solutions is magnesium nitrate, optionally further including a water soluble, inorganic copper salt. Recently U.S. Pat No. 5,153,213 suggested use of small amounts of hydrogen peroxide or similar oxidizing agents so as to avoid the nitrate and copper salt which causes problems in certain biocide applications such as in some cosmetics.

The present invention relates to an alternate way to stabilize such dilute solutions without using inorganic metal salts or hydrogen peroxide oxidizing agent.

My invention is to provide a microemulsion of said compound(s) which is free of any inorganic metal salt. Such microemulsions are formed by mixing A. about 0.5 to about 5% by weight of at least one 3-isothiazolone selected from the group consisting of 5-chloro-2-methyl-4-isothazolin-3-one and 2-methyl-4-isothazolin-3-one;

B. water;

C. organic solvent(s) having less than 6 percent by weight solubility in water;

D. anionic surfactant(s); and

E. optionally, non-ionic surfactant(s).

The art of water-soluble 3-isothiazolones, such as CMI and MI, is quite different from that of water-insoluble, oil-soluble ones, the latter including most prominently 2-n-octyl-4-isothiazolin-3-one and 4,5-dichloro-2-n-octyl-4-isothiazolin-3-one. In the case of oil soluble 3-isothiazolones, microemulsions have been proposed by Mattox et al in U.S. Pat. No. 4,954,338 and U.S. patent application Ser. No. 08/130,614, but for a completely different objective. Mattox et al's objective was not to stabilize the biocide because they were forming microemulsions of oil soluble 3-isothiazolones which are normally stable without the need to provide metal salt stabilizers. In fact, the water soluble, inorganic salt stabilizers are not even soluble in the oil phase in which the oil soluble 3-isothiazolones usually reside.

Microemulsions are multicomponent liquid dispersion systems containing nanometer-size oil droplets in an aqueous continuous phase or nanometer-size water droplets in an oil continuous phase. These microemulsions are thermodynamically stable, optically transparent and homogeneous.

The invention also comprises a method of stabilizing the aforementioned CMI and MI compounds in dilute solutions.

The most typical dilute solutions of 3-isothiazolones comprise an approximate 3:1 mixture of 5-chloro-2-methyl-4-isothazolin-3-one and 2-methyl-4-isothazolin-3-one.

The compositions of the invention comprise a 0.5 to 5% by weight based on the microemulsion composition of at least one 3-isothiazolone selected from the group consisting of CMI and MI. It is preferred that the compositions have from about 1 to about 2% 3-isothiazolone by weight.

Organic solvents useful in the compositions of the invention are any which have less than about 6% by weight solubility in water, do not destabilize the 3-isothiazolone, and are able to form microemulsions with the surfactants used. Solvents which have less than about 4% by weight solubility in water are preferred. Suitable solvents include, for example, benzyl alcohol; phenoxyethanol; toluene; mixtures of alkyl benzenes, such as mixtures of trimethylbenzene, ethyhnethylbenzene, solvent naphtha, and the like; ketones, such as diisobutyl ketone; esters, such as butyl acetate and benzyl acetate; and xylene. Phenoxyethanol and benzyl alcohol are preferred.

Generally, the amount of organic solvent useful in the compositions of the invention is from about 2 to about 20% by weight based on the microemulsion composition. Preferred amounts of solvent are from about 5 to about 15% by weight. The amount of solvent used depends upon the concentration of the 3-isothiazolone desired in the microemulsion. More solvent is required as the concentration of the 3-isothiazolone in the microemulsion is increased.

One or more anionic surfactants may be used alone or in combination with one or more non-ionic surfactants to yield the compositions of the invention. When anionic and non-ionic surfactants are used, it is preferred that the ratio of anionic surfactant(s) to non-ionic surfactant(s) be 40:60 to 45:55. Preferred compositions of the invention comprise one or more anionic surfactants and one non-ionic surfactant. Compositions comprising one anionic surfactant are most preferred.

The total amount of surfactant present in the compositions of the invention is from about 3 to about 30% by weight based on the microemulsion composition. It is preferred that the total amount of surfactant(s) be from about 10 to about 20% by weight. The amount of surfactant used depends upon the amount of solvent and 3-isothiazolone desired in the microemulsion composition. More surfactant is required as the concentration of the organic solvent in the microemulsion is increased.

Suitable anionic surfactants useful in the compositions of the invention include, for example, calcium alkylaryl sulfonate; diamyl ester of sodium sulfosuccinic acid; ammonium laureth sulfate; free acid of a complex organic phosphate ester; sodium laureth sulfate; and sulfated castor oil. Sodium laureth sulfate is preferred.

Suitable nonionic surfactants useful in the compositions of the invention include, for example, ethoxylated castor oil; octylphenol ethoxylate; ethoxylated $C_{12}$ alcohol; and polysorbate 80.

I have found that stability of the biocide compound(s) in the compositons of this invention is further improved by including one or more additional organic stabilizers. Suitable additional organic stabilizers include, for example, butylated hydroxytoluene ("BHT"), hydroquinone ("HQ"), propyl gallate, and copper octoate. These additional organic stabilizers can be used in an amount of from about 0.1 to about 5% by weight based upon the microemulsion composition. Preferred amounts of additional organic stabilizer are from about 0.5 to about 1% by weight. It is preferred that at least one additional organic stabilizer be used in the compositions of the invention. BHT is most preferred, and a mixture of BHT and HQ is especially preferred.

The preferred compositions of the invention comprise 1 to 2% by weight 3-isothiazolone, 5 to 15% by weight organic solvent, 10 to 20% by weight surfactant(s), 1% additional organic stabilizer, the remainder being water.

The compositions of the invention may be prepared by mixing 3-isothiazolone, water, organic solvent and surfactant in any order. When additional organic stabilizers are used, it is preferred that the additional organic stabilizer be dissolved in the organic solvent prior to preparation of the microemulsions. It is further preferred that surfactant and water be combined prior to combining with organic solvent containing additional organic stabilizer or that surfactant and organic solvent containing additional organic stabilizer be combined prior to combining with water.

Uses of these stabilized biocides are typically at any locus subject to contamination by bacteria, yeast, fungi, or algae. Typically, loci are in aqueous systems such as cooling water systems, laundry rinse water, oil systems such as cutting oils, lubricants, oil field waters and the like, where microorganisms need to be killed or where their growth needs to be controlled. However, these stabilized biocides may also be used in all applications for which known biocidal compositions are useful; preferred utilities of the compositions of the invention are to protect wood, latex, adhesives, glues, paper, textiles, leather, plastics, cardboard, caulking, feed, cosmetics, e.g. shampoos, conditioners, lotions, and creams; household products, e.g. dish detergents, floor waxes, cleaning products; etc.

It is known in the art that the performance of biocides may be enhanced by combination with one or more other biocides. Thus, other known biocides may be combined advantageously with the compositions of this invention.

Various adjuvants can be added to the compositions of the invention. Suitable adjuvants include, for example, antifoam agents, such as the commercially available silicone antifoam emulsions; antifreeze agents, such as propylene glycol, urea, and the like; wetting agents; thickeners; defoamers; and the like.

The least stable of the aforementioned biocide compounds is CMI, and testing for stability of that compound is most relevant. In most cases, compositions according to this invention comprising CMI are stable enough that no more than 40% of CMI is degraded after 1 week storage at 55° C.

The 3-isothiazolone used in each of the following examples was an approximate 3:1 by weight mixture of CMI and MI. All percentages are by weight. Samples were analyzed for CMI remaining by reverse phase HPLC with UV detection. Samples were considered stable when they did not phase separate and at least 60% CMI remained after 1 week of storage at 55° C. Samples which were not analyzed ("NA") had phase separated.

EXAMPLE 1

In the following examples, all samples were stored in an oven at 55C. Samples that did not phase separate after 0, 1, 2, and 3 weeks storage were analyzed by HPLC with UV detection. Samples which phase separated were not analyzed. Three stock solutions of 20% BHT by weight were prepared in 30 ml. glass vials by adding 4 g. of BHT to each of 3 vials followed by adding 16 g. of benzyl alcohol, phenoxyethanol, or xylenes. The stock solutions were heated to dissolve the BHT.

Solvents

A=Benzyl Alcohol/BHT stock solution
B=Phenoxyethanol/BHT stock solution
C=Xylene
D=Xylene/BHT stock solution
E=Deionized Water
F=Benzyl alcohol
G=Phenoxyethanol Surfactants A. Nonionic 1=ethoxylated castor oil (100% active)
2=octylphenol ethoxylate (100% active)
3=ethoxylated $C_{12}$ alcohol (100% active)
4=oleate esters of sorbitol and sorbitol anhydrides, condensed with approximately 20 moles of ehthylene oxide ("polysorbate 80") (100% active)

B. Anionic

5=calcium alkylaryl sulfonate (60% active)
6=diamyl ester of sodium sulfosuccinic acid (100% active)
7=ammonium laureth sulfate (60% active)
8=free acid of a complex organic phosphate ester (100% active)
9=sodium laureth sulfate (60% active)
10=sulfated castor oil (70% active)

EXAMPLE 2

Microemulsions were prepared using the solvents and surfactants from Example 1. To 30 ml. glass vials or 10 ml. glass test tubes were added 15% surfactant(s), 10% solvent, 3.13% 3-isothiazolones, and 71.87% deionized water. Samples were capped, mixed and stored at 55° C. prior to analysis.

| | | % CMI Remaining | | |
|---|---|---|---|---|
| Solvent | Surfactant (%) | 1 week | 2 weeks | 3 weeks |
| C | 1(56)/5(24)/6(20) | 96 | 75 | 8 |
| D | 1(56)/5(24)/6(20) | 100 | 96 | 79 |
| E # | 1(56)/5(24)/6(20) | 43 | 4 | 0 |
| E # | None | 0 | 0 | 0 |

# = Comparative; not microemulsions

The example above shows that CMI is more stable when in a microemulsion than when in water or a surfactant and water mixture. This example also shows that the stability of CMI in a microemulsion is further improved by the addition of a second stabilizer, such as BHT (Solvent D).

EXAMPLE 3

Microemulsions were prepared using the solvents and surfactants from Example 1. To 30 ml. glass, screw cap vials were added 20% surfactant(s), 10% solvent, 1.5% 3-isothiazolones, and 68.5% deionized water. Samples were capped, mixed and stored at 55° C. prior to analysis. These data are reported below.

| Solvent | Surfactant (%) | % CMI Remaining | |
|---|---|---|---|
| | | 1 week | 2 weeks |
| G | 1(12)/9(8) | 95 | NA |
| F | 1(12)/9(8) | 95 | NA |
| G | 9(20) | 90 | 52 |

EXAMPLE 4

Microemulsions were prepared using the solvents and surfactants from Example 1. To 30 ml. glass vials or 10 ml. glass test tubes were added 10% surfactant, 5% solvent, 1.55% 3-isothiazolones, and 83.45% deionized water. Samples were capped, mixed and stored at 55° C. prior to analysis.

| Solvent | Surfactant (s) | % CMI Remaining | |
|---|---|---|---|
| | | 1 Week | 2 Week |
| A | 1(56)/5(24)/6(20) | 100 | NA** |
| B | 1(56)/5(24)/6(20) | 100 | 99 |
| A | 7(100) | 81 | 87 |
| B | 7(100) | 69 | 59 |
| A | 3(60)/9(40) | 81 | 78 |
| A | 2(60)/9(40) | 77 | 90 |
| B | 2(60)/9(40) | 100 | 45 |
| B | 1(60)/8(40) | 100 | NA |
| A | 1(60)/8(40) | NA | NA |
| B* | 3(60)/9(40) | 40 | 27 |
| A | 3(50)/9(50) | NA | NA |
| B | 3(50)/9(50) | NA | NA |
| A | 2(50)/9(50) | NA | NA |
| B | 2(50)/9(50) | NA | NA |
| A | 3(70)/9(30) | NA | NA |
| B | 3(70)/9(30) | NA | NA |
| A | 2(70)/9(30) | NA | NA |
| B | 2(70)/9(30) | NA | NA |
| A | 3(60)/10(40) | NA | NA |
| B | 3(60)/10(40) | NA | NA |

*= this experiment does show substantial improvement over water solutions, but appears inconsistent compared to the other microemulsion examples

EXAMPLE 5

The effect of adding an additional stabilizer to a microemulsion was tested. Microemulsions containing BHT were prepared as in Example 3, except that the percent water was varied and HQ was added. Samples were capped and mixed prior to analysis and storage. The results are reported below.

| Solvent | Surfactant (%) | HQ (%) | Water (%) | % CMI Remaining | | |
|---|---|---|---|---|---|---|
| | | | | 1 week | 3 weeks | 4 weeks |
| A | 3(60)/9(40) | 0.25 | 83.20 | 97 | 98 | 97 |
| A | 3(60)/9(40) | 0.10 | 83.35 | 100 | 98 | 98 |
| A | 3(60)/9(40) | 0.05 | 83.40 | 89 | NA | NA |
| A# | 3(60)/9(40) | 0 | 83.45 | 76 | NA | NA |

= Comparative

The data clearly show the combination of BHT and HQ in a microemulsion has a superior stabilizing effect when compared to BHT alone.

EXAMPLE 6

Microemulsions were prepared using dilute BHT stock solutions and the CMI stability evaluated. A 10% BHT in phenoxyethanol stock solution was prepared by combining 2 g. BHT with 18 g. phenoxyethanol in a 30 ml screw cap glass vial. The vial was capped and shaken until the BHT had dissolved. Six microemulsion samples were prepared in 30 ml. screw cap glass vials using surfactants from Example 1 by adding to each sample vial 20% surfactant(s), 10% BHT stock solution, and 1.55% 3-isothiazolone, the remainder being deionized water. Three of the samples also contained 0.10% HQ. The samples were capped, mixed and stored at 55° C. The samples were analyzed at various time points for the percentage of CMI remaining.

| Surfactant | HQ | % CMI Remaining | | | |
|---|---|---|---|---|---|
| | | 1 Week | 2 Weeks | 3 Weeks | 4 Weeks |
| 1(60)/9(40) | No | 96 | 94 | 90 | NA |
| 1(60)/7(40) | No | 96 | 92 | 89 | NA |
| 4(60)/9(40) | No | 88 | 52 | 0 | NA |
| 1(60)/9(40) | Yes | 98 | 98 | 98 | NA |
| 1(60)/7(40) | Yes | 99 | 98 | 100 | 98 |
| 4(60)/9(40) | Yes | 100 | 98 | 98 | 98 |

EXAMPLE 7

Microemulsions were prepared using dilute propyl gallate stock solution and the CMI stability evaluated. A 10% propyl gallate in phenoxyethanol stock solution was prepared in a 30 ml. glass, screw cap vial by combining 1.0 g. propyl gallate with 9.0 g. phenoxyethanol. The vial was capped, heated, and shaken until the propyl gallate had dissolved. Five microemulsion samples, labeled 7-1 to 7-5, were prepared in 30 ml. glass, screw cap vials by combining surfactants from Example 1 with 10% propyl gallate stock solution (to give 1% propyl gallate in the final microemulsion), 1.5% 3-isothiazolone, and water. The amounts of surfactants and water are shown below. Two microemulsion samples, labeled 7-6 and 7-7, were prepared in 30 ml. glass, screw cap vials by combining surfactants from Example 1 with 10% phenoxyethanol (containing no propyl gallate), 1.5% 3-isothiazolone, and water, and used as a comparison.

The microemulsion samples were capped, shaken, and stored at 55° C. Samples were analyzed for % CMI remaining after 1 and 2 weeks.

| Sample | % Water | Surfactant 1 (%) | Surfactant 2 (%) | % CMI Remaining | |
|---|---|---|---|---|---|
| | | | | 1 Week | 2 Weeks |
| 7-1 | 73.5 | 4(9.0) | 9(6.0) | 94 | 91 |
| 7-2 | 68.5 | 4(12.0) | 9(8.0) | 97 | 92 |
| 7-3 | 73.5 | 1(9.0) | 9(6.0) | 98 | NA |
| 7-4 | 68.5 | 1(12.0) | 9(8.0) | 98 | NA |
| 7-5 | 68.5 | 9(20.0) | — | 114 | 102 |
| 7-6# | 68.5 | 1(12.0) | 9(8.0) | 95 | NA |
| 7-7# | 68.5 | 9(20.0) | — | 90 | 52 |

= Comparative

These data show that the stability of CMI in a microemulsion is further improved by the addition of propyl gallate.

What is claimed is:

1. A microemulsion consisting essentially of:
   A. 0.5 to 5% by weight of at least one 3-isothiazolone selected from the group consisting of 5-chloro-2-methyl-4-isothazolin-3-one and 2-methyl-4-isothazolin-3-one;
   B. water;
   C. 2 to 20% by weight organic solvent(s) having less than 6 percent by weight solubility in water; and
   D. 3–30% by weight surfactant(s) consisting of anionic surfactant(s) and,
   optionally, non-ionic surfactant(s).

2. Composition according to claim 1 wherein A. is a mixture of 5-chloro-2-methyl-4-isothazolin-3-one and 2-methyl-4-isothazolin-3-one.

3. Composition according to claim 1 wherein said solvent(s) is selected from the group consisting of benzyl alcohol, phenoxyethanol, toluene, alkyl benzenes, diisobutyl ketones, esters, and xylene; said nonionic surfactant is selected from the group consisting of ethoxylated castor oil; octylphenol ethoxylate; ethoxylated $C_{12}$ alcohol; and polysorbate 80; and said anionic surfactant is selected from the group consisting of calcium alkylaryl sulfonate; diamyl ester of sodium sulfosuccinic acid; ammonium laureth sulfate; free acid of a complex organic phosphate ester; sodium laureth sulfate; and sulfated castor oil.

4. Composition according to claim 1 wherein said composition further includes one or more stabilizer compounds selected front the group consisting of butylated hydroxytoluene, hydroquinone, and propyl gallate.

5. Composition according to claim 1 wherein said compound(s) A is stable to the extent that: A comprises 5-chloro-2-methyl-4-isothazolin-3-one and no more than 40% of said 5-chloro-2-methyl-4-isothazolin-3-one is degraded after 1 week storage at 55° C.

6. Composition according to claim 1 wherein C is benzyl alcohol or phenoxyethanol and said composition further includes a mixture of butylated hydroxytoluene and hydroquinone stabilizers, the ratio of C to said further included stabilizers being 70:30 to 90:10.

7. Composition according to claim 1 wherein each of said ingredients is present in the following percentages by weight:
   A=1 to 2%;
   C=5 to 15%;
   D and E together=10 to 20%.

8. Method of stabilizing a 3-isothiazolone compound selected from the group consisting of 5-chloro-2-methyl-4-isothazolin-3-one and 2-methyl-4-isothazolin-3-one comprising preparing a microemulsion of said compound(s) by mixing said compound(s) with water; organic solvent(s); anionic surfactant(s); optionally, non-ionic surfactant(s); and optional additional compounds exclusive of inorganic metal salt, in proportions suitable to form a microemulsion, said proportions being 0.5 to 5% by weight of said compound(s); 2 to 20% by weight of said organic solvent(s); and 3 to 30% by weight of surfactant(s).

* * * * *